United States Patent
Maxwell et al.

(10) Patent No.: US 6,168,631 B1
(45) Date of Patent: Jan. 2, 2001

(54) SUBTALAR IMPLANT SYSTEM AND METHOD FOR INSERTION AND REMOVAL

(75) Inventors: Jerry R. Maxwell, Edmond, OK (US); Steven P. Brancheau, Greenville, TX (US)

(73) Assignee: Kinetikos Medical, Inc., San Diego, CA (US)

( * ) Notice: Under 35 U.S.C. 154(b), the term of this patent shall be extended for 0 days.

(21) Appl. No.: 08/919,558

(22) Filed: Aug. 29, 1997

(51) Int. Cl.[7] ........................................ A61F 2/42
(52) U.S. Cl. .................... 623/21.18; 623/17.11; 623/18.11; 623/21.11
(58) Field of Search .................. 623/17, 17.11, 623/18.11, 21.11, 21.18

(56) References Cited

U.S. PATENT DOCUMENTS

| | | | |
|---|---|---|---|
| 5,360,450 | * 11/1994 | Giannini | 623/21 |
| 5,741,253 | * 4/1998 | Michelson | 623/17 |
| 5,766,253 | * 6/1998 | Brosnahan | 623/17 |
| 5,776,196 | * 7/1998 | Matsuzaki | 623/17 |
| 5,785,710 | * 7/1998 | Michelson | 623/17 |

OTHER PUBLICATIONS

The Valenti STJ Arthroereisis Implant: a Ten–Year Retrospective Study, Brancheau et al. Chapter 8, pp. 44–53;.
Valenti Arthroereisis and Talonavicular Fusion for Collapsing Pes Valgus in the Adult Maxwell, pp. 81–84.

* cited by examiner

Primary Examiner—Michael J Milano
(74) Attorney, Agent, or Firm—Baker & Maxham

(57) ABSTRACT

A system, method, and tools including a subtalar arthroereisis implant for use in reducing calcaneal eversion, blocking anterior and inferior displacement of the talus, and blocking excessive pronation and the resulting sequelae, while allowing normal subtalar joint motion. The method includes in the preferred system inserting a probe to slightly dilate the tarsal canal, inserting a cannulated "sizer" having a guide element placed therein into the dilated sinus tarsi resulting in the guide element being inserted through the tarsal canal. The sizer is removed, leaving the guide element in place. Once the implant has been sized, a trial implant in inserted by placing a conically shaped "nose cone" on the guide element ahead of the implant. Once the trial implant is in place, sizing is checked, the trial implant is removed, and the actual implant is inserted following generally the same procedure as for the trial implant. Most of the tools which must be inserted into the tarsal canal are cannulated, such that the tools, and the implant itself, can be guided through the canal by a guide element.

20 Claims, 4 Drawing Sheets

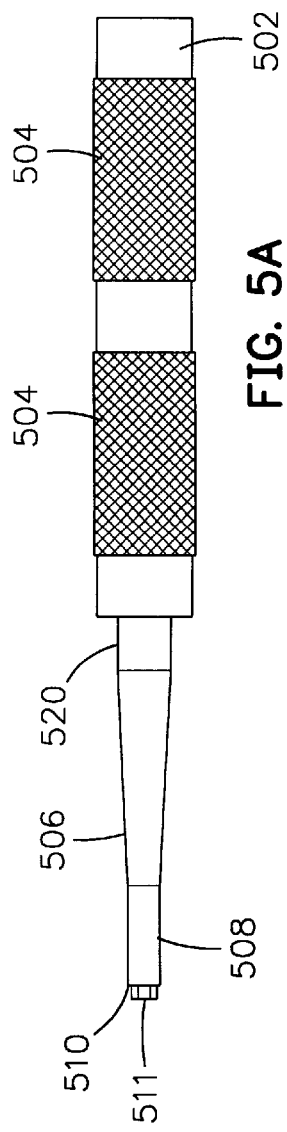
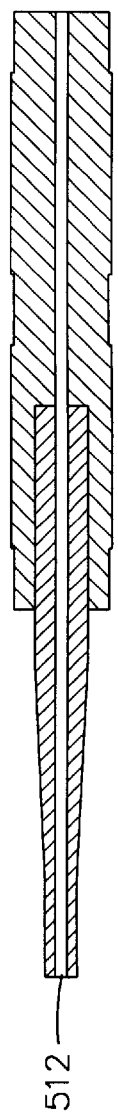
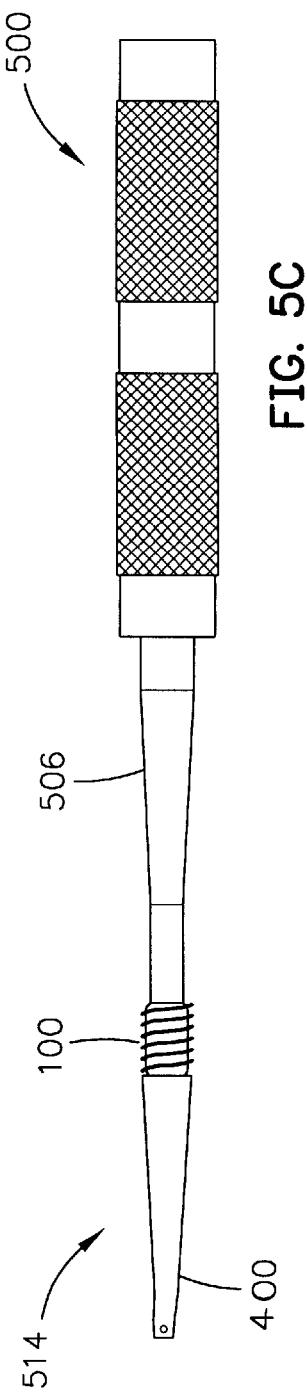
FIG. 5A
FIG. 5B
FIG. 5C

SUBTALAR IMPLANT SYSTEM AND METHOD FOR INSERTION AND REMOVAL

BACKGROUND OF THE INVENTION

1. Field of the Invention

This invention relates to methods and devices for correcting foot disorders, and more particularly to methods and devices for correction of pediatric pes valgus and adult posterior tibial dysfunction deformity by reducing calcaneal eversion.

2. Description of Related Art

As early as 1946, surgeons have been attempting to apply the arthroereisis concept to the subtalar joint to correct severe collapsing pes valgo planus. One early method was to remedy abnormal excursion of the talus on the calcaneus with the talus contacting the floor of the sinus tarsi by using an "abduction block" procedure. During the abduction block procedure, a wedge-shaped bone graft was impacted into the anterior leading edge of the posterior facet of the calcaneus. Impacting such a bone graft prevented excessive inferior displacement of the talus upon the calcaneus, thus limiting the amount of excess pronation of the subtalar joint.

A pronation limiting osteotomy inter form of a lateral opening wedge of the posterior facet was developed for treatment of "flatfoot" in cereal palsy patients in 1964. In order to prevent interfering with subtalar joint motion, a wedge-like bone graft was used to improve the weight-bearing alignment of the calcaneus. In 1970, an accessory bone graft placed in the sinus tarsi was developed as a corrective procedure. Later, the bone graft was replaced with a silastic plug. As early as 1976, a high molecular weight polyethylene plug was developed. The plug is cemented into the calcaneal sulcus against a resected portion of the posterior calcaneal facet. This procedure, known as "STA-peg" (subtalar arthroereisis-peg), is today a commonly used subtalar joint arthroereisis procedure. STA-peg does not block excessive pronation, but rather alters the axis of motion of the subtalar joint.

Also in 1976, a high-molecular-weight, polyethylene, threaded device known as a "Valenti Sinus Tarsi Arthroereises Device" was invented. The procedure used implant the Valenti device is commonly referred to as the "Valenti" procedure. Unlike the STA-peg procedure, the Valenti procedure is an extra-articular procedure that involves placing the Valenti device into the sinus tarsi to block the anterior and inferior displacement of the talus. Such placement of the Valenti device does not restrict normal subtalar joint motion, but does block excessive pronation and resulting sequelae. The Valenti device has a frusto-conical shape and threads on the outer surface of the device which allow it to be screwed into the sinus tarsi. As a consequence of the shape of the Valenti device, the greater the penetration of the device into the sinus tarsi, the more the sinus is dilated and the more calcaneal eversion is eliminated.

However, several problems reduce the desirability of the Valenti procedure and device. For example, the Valenti device is manufactured from polyethylene which must be gas-sterilized prior to use and which allows the device to deform under the compressive pressure to which it is subjected under normal post-operative conditions. Furthermore, because of its fresto-conical shape and the manner in which it is inserted, it is difficult to precisely locate the device and ensure that the proper amount of calcaneal eversion has been eliminated. Still further, it is generally difficult to locate the device properly within the tarsal canal because the implant must be threaded at least 3 to 5 millimeters medial to the most lateral aspect of the posterior facet for correct placement. Because of its polyethylene construction, the device cannot be imaged using radiography (X-ray) to determine whether the proper position has been achieved.

Accordingly, it is an object of the present invention to provide an implant which can be easily located within the tarsal canal, which would not deform under post-operative compressive forces, which would ensure the proper amount of calcaneal eversion has been eliminated after insertion of the implant, and which can be imaged using radiography to determine whether the implant has been properly positioned during the procedure.

SUMMARY OF THE INVENTION

The present invention is a system including a subtalar arthroereisis implant for use in reducing calcaneal eversion, blocking anterior and inferior displacement of the talus, and blocking excessive pronation and the resulting sequelae, while allowing normal subtalar joint motion. The present invention also includes instruments and a method for inserting the implant.

The implant is preferably a generally cylindrical, or barrel shaped device having threads on the exterior surface. In addition, the implant preferably has slots formed in the threaded surface. The slots make the implant resilient and allow the implant to dissipate forces impacted upon the implant. Accordingly, stresses encountered by the implant are reduced. Another benefit of the slots and threads is that fibrous tissue will readily attach to the implant, thus aiding in securing the implant within the sinus tarsi. The implant is preferably fabricated from a titanium based alloy. Thus, the implant can be imaged in radiographs, making proper placement of the implant more discernable. Furthermore, the use of a titanium based alloy reduces the likelihood that the implant will deform under normal post-operative compressive forces.

In accordance with the preferred embodiment, the implant generally has a uniform radius along a central longitudinal axis. This allows strict control over the amount of calcaneal eversion to be eliminated and is not directly related to the location of the implant within the tarsal canal. That is, if the implant is properly located within the sinus tarsi, then the exact number of rotations of the implant will not affect the amount of dilation that occurs as a result of the implant. In addition, the implant is preferably cannulated to allow the implant to be mounted upon a guide device for positioning.

In the preferred system, most of the instruments which must be inserted into the tarsal canal are cannulated, such that the instruments, and the implant itself, can be guided through the canal by a guide device. A selection of differently sized implants are available to the surgeon performing the implantation. To begin the procedure, the tarsal canal is exposed by applying a scalpel or laser to the site, or by any other technique which allows access to the tarsal canal. A probe is used to slightly dilate the tarsal canal. Once the tarsal canal has been dilated by insertion of the probe, a first cannulated "sizer" is inserted into the sinus tarsi. Sizers preferably range from approximately 6 mm to approximately 12 mm, but other sized sizers may be used. The sizers are used to estimate the proper size implant. A guide device is inserted through the tarsal canal. The device is preferably relatively thin and thus may be inserted through the tarsal canal relatively easily. The guide device is placed into the cannulated sizer and inserted into the sinus tarsi together with the sizer. The sizer is removed, leaving the guide device in the patient.

Once the proper size implant has been estimated, a trial implant is preferably inserted into the sinus tarsi. In accordance with the preferred embodiment, the trial implant is not slotted in order to allow for ease of cleaning and resterilization. In addition, the trial implant may be manufactured from a material which is less costly than the titanium alloy which is preferably used for the actual implant.

To insert the trial implant, a generally conical shaped "nose cone" is preferably placed on the guide device to clear the sinus tarsi ahead of the implant. The trial implant is placed on the guide device directly behind the nose cone. A cannulated hex head driver, which mates to the trial implant, is preferably used to bring the cone and the insert into contact with the sinus tarsi, allowing the surgeon to screw the trial implant into place within the sinus tarsi.

Once the trial implant is in place, a determination can be made as to whether the implant is properly sized. If so, then the trial implant is removed and an actual implant of the same size is inserted following generally the same procedure as described for the trial implant. The nose cone is then removed from the tarsal canal through an incision on the medial aspect of the patient's foot. Intraoperative radiographs may be taken of both the trial implant and the actual implant to determine whether the placement is satisfactory.

The inventive system also includes a nose cone extractor which is used to remove the nose cone through an incision in the medial aspect of the patient's foot. The nose cone preferably has a small hole disposed near the distal end of the nose cone. The hole is sized to mate with a tooth on the jaw of the nose cone extractor. Thus, once the nose cone protrudes through the medial aspect of the patient's foot, the extractor may be used to fully remove the nose cone, leaving the implant in place. Thereafter, the tarsal canal is rendered unexposed by stitching, stapling, grafting, compressively packing or otherwise closing the surgical area.

The present invention satisfies the need for a subtalar arthroereisis implant that does not post-operatively substantially permanently deform over time, that may be sterilized by autoclave, that is guided into place by a guide device, that can be individually sized for each application, and that utilizes exterior channels to dissipate forces impacted upon the implant and thereby reduce implant stress, yet which allows for improved anchoring due to interstitial fiber growth.

Moreover, applicant's invention simplifies the positioning of the implant within the sinus tarsi because of the uniform radius of the sized implant and the ability to verify the proper positioning by radiography.

BRIEF DESCRIPTION OF THE DRAWINGS

The objects, advantages, and features of this invention will become readily apparent in view of the following description, when read in conjunction with the accompanying drawings, in which:

FIG. 5a shows a side view of an insertion instrument in accordance with a preferred embodiment of the present invention;

FIG. 5b shows a cross-sectional view of the insertion instrument pictured in FIG. 5a, in accordance with a preferred embodiment of the present invention; and FIG. 5c shows an assembled view of the nose cone of FIG. 4a, the implant of FIGS. 1a and 1b, and the insertion instrument of FIGS. 5a and 5b, in accordance with a preferred embodiment of the present invention.

Lastly, like reference numbers and designations in the various drawings refer to like elements.

DETAILED DESCRIPTION OF THE INVENTION

Throughout this description, the preferred embodiment and examples shown should be considered as exemplars, rather than limitations on the present invention.

Figure 1A:
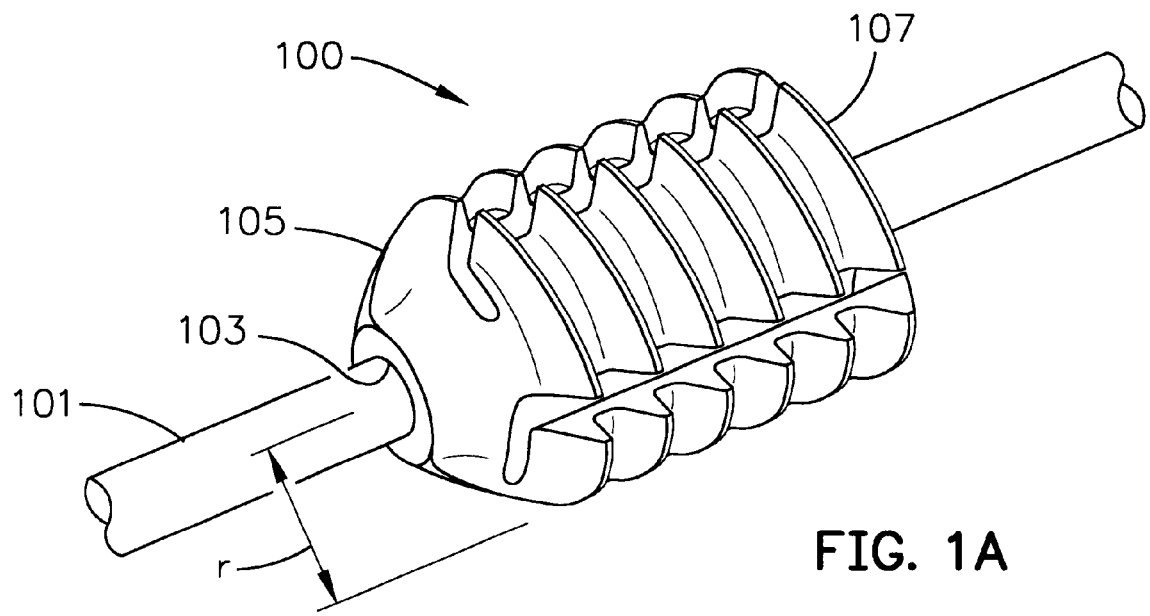
FIG. 1a shows a perspective view of an implant in accordance with a preferred embodiment of the present invention.

The present invention comprises a subtalar arthroereisis implant system and method for implanting a subtalar arthroereisis implant which blocks the anterior and inferior displacement of the talus, thus allowing normal subtalar joint motion while blocking excessive pronation and the resulting sequela. FIG. 1a is a perspective view of one preferred embodiment of an implant 100 mounted on a guide element 101 in accordance with the present invention. The guide element 101 passes through a bore 103 which is substantially coaxial with the longitudinal axis of the implant 100. The implant is preferably essentially of uniform radium r about the longitudinal axis. However, in accordance with the preferred embodiment, the distal end 105 of the implant 100 is generally rounded. In contrast, the proximal end 107 preferably ends generally abruptly along a plane that is normal to the longitudinal axis.

Figure 1B:
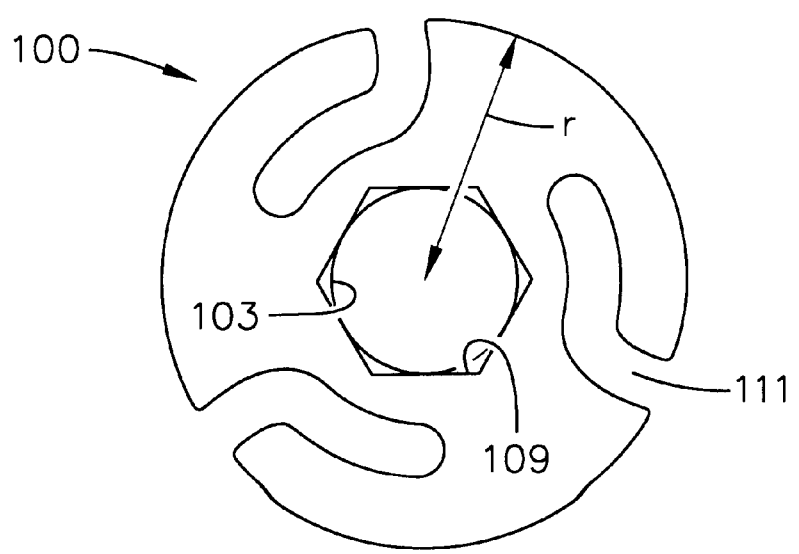
FIG. 1b shows a proximal end plan view of the implant shown in FIG. 1a, in accordance with a preferred embodiment of the present invention.

FIG. 1b is a proximal end plan view of the implant 100 shown in FIG. 1a. At the proximal end of the bore 103, a hexagonal recess 109 is formed to allow the implant to be mated with a hex head driver. Although a hex head configuration is preferred, an alternative embodiment may have a square, rectangular, octagonal or similar configuration. In accordance with one embodiment of the present invention, the hexagonal recess 109 has a depth of approximately one quarter the length of the implant in order to allow the hex head driver to be securely seated within the recess 109. However, this depth may be varied so long as the driver head can be securely seated.

The implant preferably has three slots 111, equally spaced apart and formed generally parallel to the longitudinal axis of the implant. Alternatively, the implant may have more or less than three slots. The slots 111 allow the implant to slightly deform when compressive forces are applied to the implant. As shown in FIG. 1b, the slots 111 terminate within the body of the implant 100 and do not extend as far as bore 103. The implant is preferably machined from a block of titanium based alloy such as Ti-6-AL-4V ELI, which conforms to ASTM Standard F-136-84. However, casting techniques, such as investment, blow, thin walled, etc., may be used. Furthermore, a cobalt-based alloy, composite, or other comparable material having generally the same properties as the titanium based alloy may be substituted. The implant is also preferably externally threaded to allow insertion by rotating the implant using a hex head driver which engages the implant in a recess 109. The threads are preferably 2.53 mm, 0.100 pitch, standard "V" type threads, but may vary. Implants preferably are made over a range of sizes. For example, in the system of the preferred embodiment, four implants are provided which range in size from 6 mm to 12 mm, each separated from the other by 2 mm increments. The size of the implant refers to the threaded diameter. The bore is preferably 2.1 mm in diameter and extends the full length of the implant's preferred length of approximately 15 mm. In accordance with one embodiment of the present invention, the implant may be tumble deburred in a plastic media for 5 hours to ensure rounded edges. Once deburred, the implant is preferably passivated, anodized, and the size is laser marked upon the implant.

Figure 2A:
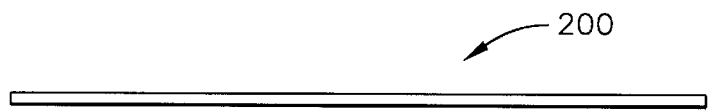
FIG. 2a shows a side view of a guide element in accordance with a preferred embodiment of the present invention.
Figure 2B:
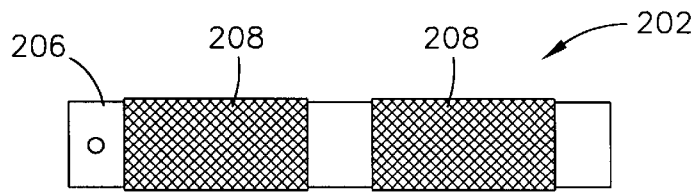
FIG. 2b shows a side view of a guide handle in accordance with a preferred embodiment of the preferred invention.
Figure 2C:
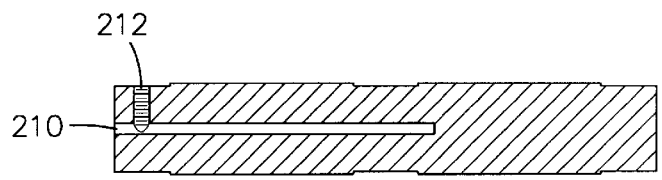
FIG. 2c shows a cross-sectional view of the handle shown in FIG. 2b, in accordance with a preferred embodiment of the present invention.

FIG. 2a shows a guide element 200. Preferably the guide element 200 is a generally rigid pin shaped device made of a 17-4 alloy stainless steel. However, any material, including composites, having generally similar rigidity to that of the 17-4 alloy may be substituted. FIGS. 2b and 2c illustrate in a side and a cross-sectional view, respectively, a preferred guide handle 202 used to insert the guide element 200 shown in FIG. 2a. The guide handle 202 preferably has a round elongated body 206 with knurly protuberances 208 extending form the outer surface forming two rings about the body 206. A bore 210 extends into the elongated body 206 from one of the body's ends and preferably terminates within the body. However, the bore may extend throughout body 206. A mechanism for securing the guide element 200 within the bore, such as a standard ball plunger 212, may be used, as may a set-screw, a quick-release pin, friction fit, press fit, or any comparable holding mechanism.

Figure 3A:
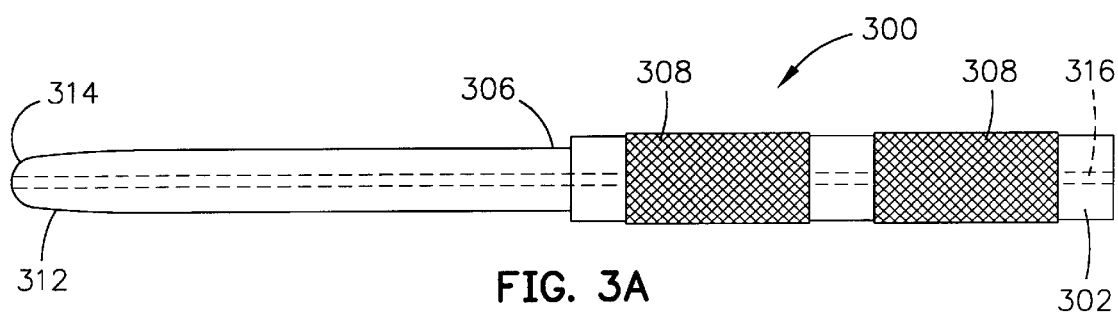
FIG. 3a shows a side view of a sizer instrument in accordance with a preferred embodiment of the present invention.
Figure 3B:
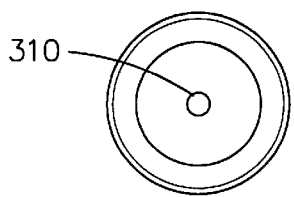
FIG. 3b shows an end view of the size instrument shown in FIG. 3a, in accordance with a preferred embodiment of the preferred invention.

FIGS. 3a and 3b illustrate a side view and an end view of one size of a cannulated sizer tool 300. Multiple sizer tools having different sizes might be used in performing the preferred method of the present invention. Preferably, the sizer tool 300 has a handle 302 with a cylindrically shaped member 304 coupled integrally thereto at its proximate end 306. The handle 302 has two knurled surfaces 308 external thereto to assist in gripping the tool. The cylindrical member 304 preferably has a generally constant radius 310, wherein the radius generally corresponds to the radius r, shown in FIG. 1a, of an implant. In the preferred embodiment, member 304 tapers at its proximal end 312 to form a blunt tip 314. A bore 316 extends substantially coaxially through the handle 302 and the member 304. The radial dimension of the bore 316 preferably generally conforms to the external dimensions of the guide device 200.

Figure 4A:
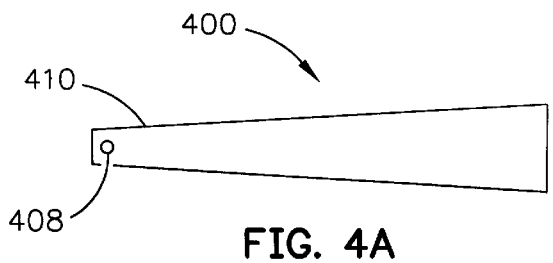
FIG. 4a illustrates a nose cone in accordance with a preferred embodiment of the invention.
Figure 4B:
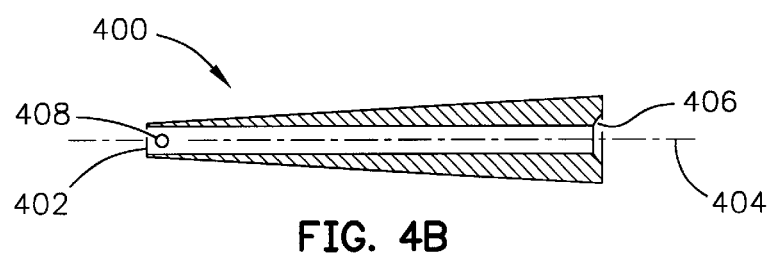
FIG. 4b shows a cross-sectional view of the nose illustrated in FIG. 4a, in accordance with a preferred embodiment of the preferred invention.

A nose cone 400 in accordance with the preferred embodiment of the present invention is shown in FIG. 4a. FIG. 4b is a cross-sectional view of the nose cone 400. A first bore 402 extends along a longitudinal axis 404 and through the cone 400. A concave recess 406 appears in the base end of the cone 400 and is sized to correspond to the generally rounded distal end 105 of the implant 100 as shown in FIG. 1a. A second bore 408 preferably positioned towards the top end 410 of the nose cone 400 passes through the body of the cone 400. The bore 408 allows the insertion of a tip 442 of a nose cone removal tool shown in FIGS. 4c and 4d for removing the cone 400 from the patient's foot.

Figures 4C, 4D:
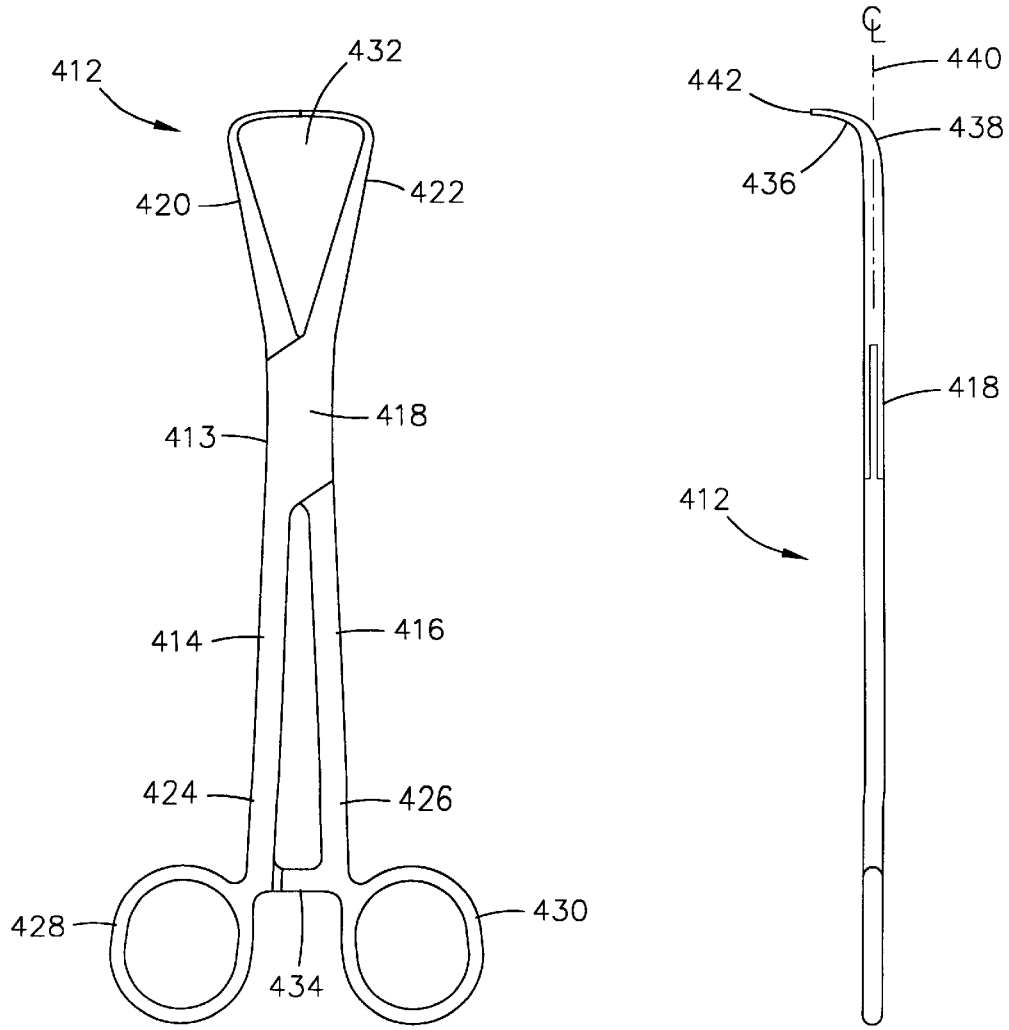
FIG. 4c shows a top view of the nose cone extractor instrument in accordance with one embodiment of the invention.
FIG. 4d shows a side view of the nose cone extractor instrument illustrated in FIG. 4c.

FIGS. 4c and 4d show a nose cone extractor tool 412 in accordance with one version of the preferred embodiment of the present invention.

The tool 412 has a body 413 having a first element 414 with a first proximal end 424 and a first distal end 420. The tool 412 also has a second element 416 having a second proximal end 426 and a second distal end 422. A first handle 428 is attached to the first element 414 at the first proximal end 424. Similarly, a second handle 430 is attached to the second element 416 at the second proximal end 426.

The first element 414 and the second element 416 are rotatably attached by an attachment means 418. The attachment means may be any type of attachment device such as a bolt, true pin, lock pin, or any such device which allows rotation of the elements attached by the attachment devices. The first distal end 420 of the first element 414, and the second distal end 422 of the second element 416 cooperate to form a jaw 432. Reliefs (not shown) may be positioned in the jaw and cooperate with the jaw 432 in grasping a nose cone member. Generally, when a force is applied to the handles 428 and 430 which causes the handles to move away from each other, the first element 414 and the second element 416 rotate about attachment means 418, thereby causing the first distal end 420 of the first element 414 to move away from the second distal end 422 of the second element 422. As the proximal ends 420 and 422 move towards one another in an arcuate motion, the first element 414 and the second element 416 rotate in opposite directions around attachment means 418. This rotation of the body elements causes the distal ends 420 and 422 to move towards one another, thereby causing jaw 432 to close. As shown in FIG. 4c, a securing means 434 may be juxtaposed to the handles 428 and 430 in order to assist in holding the handles in a secured position. In another embodiment, the securing means 434 may be located anywhere along the body 413. The securing means 434 may comprise interlocking ridges, a magnetic fastener, lock and loop material, or any other securing means capable of being released and re-secured.

FIG. 4d illustrates the curved end 438 of the tool 412. The curved end 438 comprises the first and second distal ends 422 and 420 of the first element 414 and the second element 416, respectively. The curve 436 of the curved end 438 bends substantially perpendicularly away from a longitudinal centerline 440 of the body 413. In another embodiment, the distal ends 420 and 422 are substantially straight and curve 436 is non-existent. As pictured, a tip 422 of the tool 412 may be used to engage the nose cone 400 via the bore 408 for handling of the nose cone 400.

A side view of the preferred embodiment of an insertion tool 500 is shown in FIG. 5a. A cross-sectional view of the tool 500 is shown in FIG. 5b. The tool 500 preferably has a cylindrically shaped handle 502 which has knurled protrusions 504 extending from its exterior surface. Tool 500 also has a tapered elongated member 506 internally coupled at its proximal end 520 to handle 502. Member 506 extends away from handle 502 and tapers towards its distal end 508. The distal end 508 truncates, forming a shoulder 510 having a nub 511 extending therefrom. Preferably, the nub 511 is hexagonally shaped to allow it to couple with the hexagonal recess 109 that is formed into the proximal end 103 of the implant 100, and allows mating of the implant 100 to the insertion tool 500. Although a hexagonal shape is preferred for nub 511, the nub may be of any configuration so long as it is configured as a positive mirror image of recess 109 and is capable of engaging the implant 100.

The cross-sectional view in FIG. 5*b* of the insertion tool 500 shows that a bore 512 preferably extends generally coaxially through the nub 511, the elongated member 506, and the handle 502. The bore 512 allows the insertion tool to slide onto the guide element 200 and to slide along the guide element 200 as desired. FIG. 5*c* shows the ideal assembly 514 of the nose cone 400, the implant 100, and the insertion tool 500, wherein the implant 100 is positioned upon the nub 511 of the elongated member 506 of the insertion tool 500. After being assembled, the assembly would ideally be placed onto the guide element 200 and then used as part of the system to perform the method of the current invention.

SUMMARY

A number of embodiments of the present invention have been described. Nevertheless, it will be understood that various modifications may be made without departing from the spirit and scope of the invention. For example, nose cone 400 might be made without a second bore 408 and may be serrated instead, allowing a tool designed to grasp the serrations to remove the cone. Also, the handles of the tools may be shaped to contour to the surgeon's hand; the implant or tools may be provided without a bore. Therefore, the spirit and scope of the appended claims should not be limited by the specific description of the preferred embodiments contained herein.

What is claimed is:

1. An implant for blocking anterior and inferior displacement of a talus within a patient, comprising:
    (a) a substantially cylindrical body having a longitudinal axis and a proximal end, the body being sized and shaped to fit within a sinus tarsi of a subtalar joint of the patient, with at least one slot is formed in the body, with the slot being sized and shaped to make the implant sufficiently resilient to dissipate forces impacted upon the implant in normal use;
    (b) an engagement element located at the proximal end structured to engage an insertion tool to enable rotational actuation of the implant about the longitudinal axis of the implant and thus thread the implant into place in the subtalar joint; and
    (c) threads formed about an exterior surface of the body of the implant, the threads being located to be in direct contact with tissue of the subtalar joint.

2. The implant of claim 1, further comprising threads formed about an exterior surface of the body of the implant.

3. The implant of claim 1, wherein a bore extends through the body of the implant with the bore being sized and shaped to substantially envelop a guide element when the body is placed on the guide element.

4. The implant of claim 1, wherein at least one slot is formed in the body, with the slot being sized and shaped to make the implant sufficiently resilient to dissipate forces impacted upon the implant in normal use.

5. The implant of claim 1, wherein the body of the implant is made from a titanium based alloy.

6. The implant of claim 4, wherein the slot terminates within the body of the implant.

7. The implant of claim 4, wherein the body of the implant is made from a titanium based alloy.

8. The implant of claim 4, wherein the body of the implant is made from a material that is sufficiently resilient to generally prevent severe deformation of the implant, and wherein the material allows the slot to remain essentially open under normal compressive forces experienced by the implant.

9. A method of using the implant of claim 1, comprising the steps of:
    engaging an insertion tool to the engagement element; and
    rotating the insertion tool thereby to drive the implant to rotate about the longitudinal axis into place in the subtalar joint.

10. The implant of claim 1, wherein the engagement element is formed as a polygonal recess.

11. The implant of claim 10, wherein the recess has a substantially hexagonal shape.

12. The implant of claim 1 wherein the at least one slot is sized and shaped to facilitate attachment of fibrous tissue to the implant.

13. The implant of claim 1 wherein the at least one slot is substantially parallel to the longitudinal axis.

14. The implant of claim 1 wherein the body is formed with three slots.

15. The implant of claim 14 wherein the slots are substantially equally spaced around the cylindrical body.

16. The implant of claim 1 wherein the body is formed of a material that will produce an radiograph image.

17. The implant of claim 1 wherein the body is formed by machining a block of material.

18. The implant of claim 1 wherein the threads are standard V-type threads.

19. The implant of claim 18 wherein the threads are 2.53 mm, 0.100 pitch threads.

20. The implant of claim 10 wherein the polygonal recess has a depth of approximately one quarter of a length of the implant.

* * * * *